United States Patent [19]

Bolling

[11] Patent Number: 4,943,277
[45] Date of Patent: Jul. 24, 1990

[54] RETROGRADE CORONARY SINUS CARDIOPLEGIA CANNULA AND METHOD FOR USING SAME IN HEART SURGERY

[76] Inventor: Steven F. Bolling, 3456 Daleview Dr., Ann Arbor, Mich. 48105

[21] Appl. No.: 328,228

[22] Filed: Mar. 24, 1989

[51] Int. Cl.⁵ ............................................ A61M 29/00
[52] U.S. Cl. ....................................... 604/96; 604/101; 604/49
[58] Field of Search .................. 604/96, 97, 101, 102, 604/43, 44, 45, 49, 51-54; 128/344

[56] References Cited

U.S. PATENT DOCUMENTS

| | | | |
|---|---|---|---|
| 4,601,706 | 7/1986 | Aillon | 604/102 |
| 4,733,652 | 3/1988 | Kantrowitz et al. | 604/96 |
| 4,832,028 | 5/1989 | Patel | 604/101 |
| 4,857,054 | 8/1989 | Helfer | 604/102 |

Primary Examiner—John D. Yasko
Attorney, Agent, or Firm—Harness, Dickey & Pierce

[57] ABSTRACT

A cannula is disclosed through which cardioplegia and other types of material may be inserted into a coronary sinus without the need for directly cannulating or manipulating the sinus. The cannula is inserted through the right atrial appendage of the heart, and enters the inferior vena cava while traversing the right atrium cavity. The cannula contains inflatable seals for blocking the inferior vena cava and the right atrium cavity thereby isolating a portion of the heart which contains the coronary sinus. The coronary sinus is therefore made to be the only exit from this isolated portion. Cardioplegia or the like is injected into the isolated portion for subsequent flow into the coronary sinus. Additionally, the cannula contains a plurality of passages which allow for de-oxygenated blood flowing within the superior and inferior vena cavas to enter the cannula such that the blood may be directed, by the cannula, to suitable oxygenating apparatus.

12 Claims, 3 Drawing Sheets

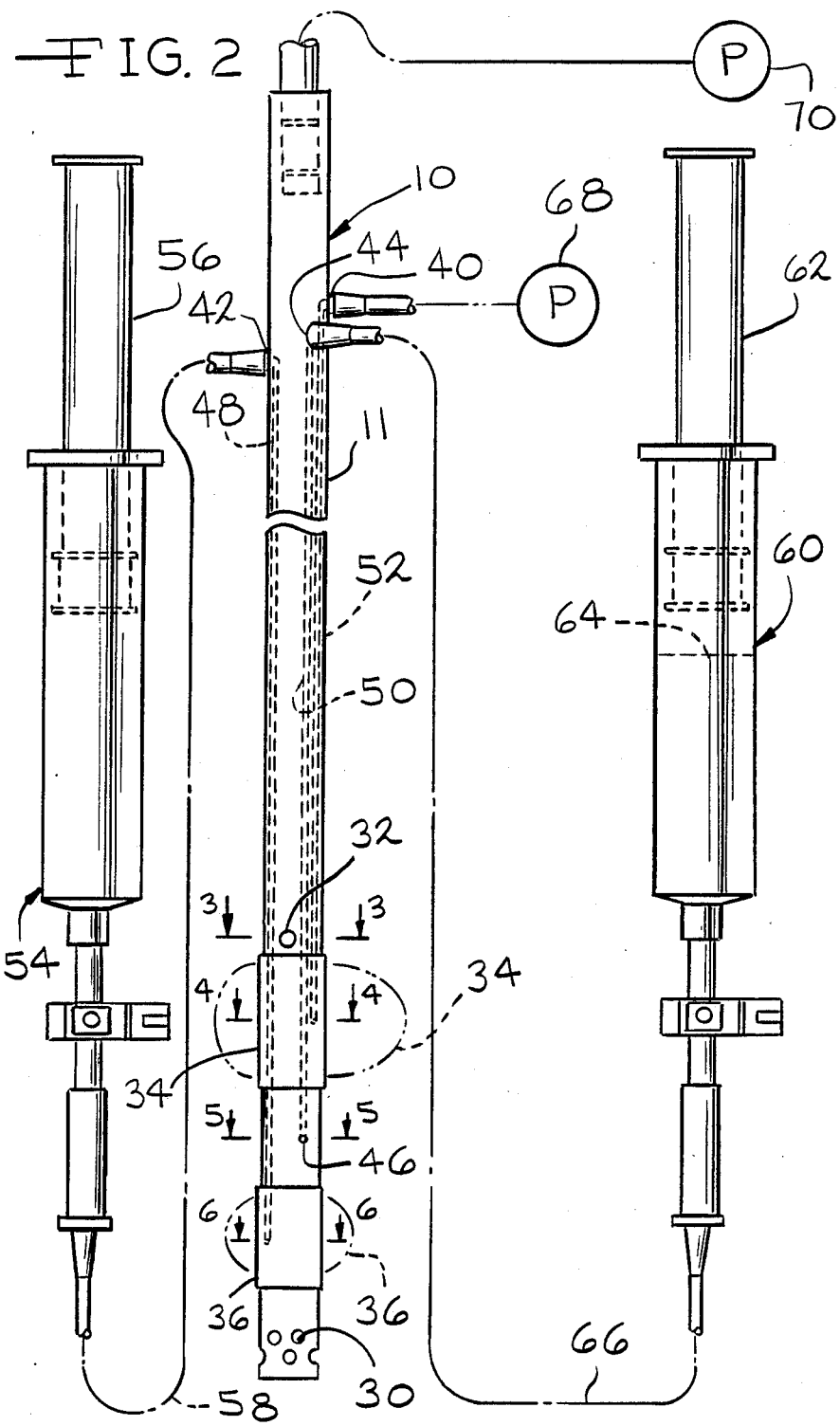

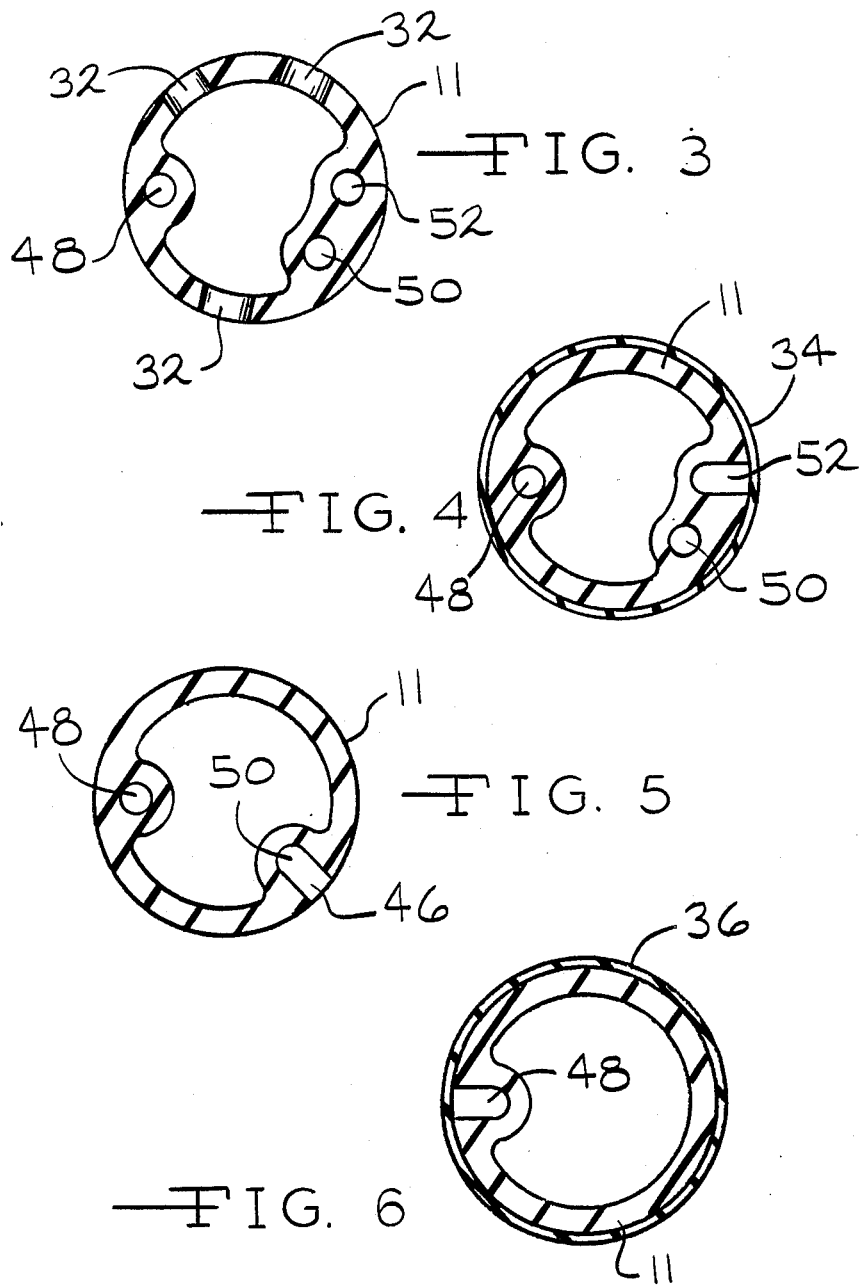

RETROGRADE CORONARY SINUS CARDIOPLEGIA CANNULA AND METHOD FOR USING SAME IN HEART SURGERY

BACKGROUND OF THE INVENTION

1. Field of the Invention

This invention relates to a method and apparatus for delivering material to the veins of the heart during open heart surgery. More particularly, this method and apparatus allows cardioplegia type material to be transported into the coronary veins through the coronary sinus of the heart such that the cardioplegia is distributed in a substantially homogenous manner throughout the heart.

2. Discussion

During open heart surgery it has been found that it is very advantageous to distribute cardioplegia type material within the coronary veins of the heart. The functions of such cardioplegia include keeping the heart cold thereby providing protection during surgery, washing away metabolic waste products, providing metabolic nutrients in order to satisfy the heart's existing energy requirements, and keeping the heart electrically quiescent. Because of these important cardioplegic functions it is known to be very desirable to have the cardioplegia evenly and completely distributed within the entire coronary vein system of the heart. This complete homogeneous distribution of cardioplegia assures that the entire heart is subject to these aforementioned favorable cardioplegia functions. A failure to homogeneously distribute cardioplegia to the heart, during surgery, is known to possibly cause a deterioration of the heart's functioning in the post operative period. Cardioplegia distribution is therefore known to possibly be a very important factor in the ability of the heart to recover from such heart surgery.

In the past, the cardioplegia was usually delivered to the arteries of the heart through the aorta root. It has been found however that this method will not always result in a truly homogeneous distribution of cardioplegia within the coronary arteries. For example, if the heart has a general coronary atherosclerosis condition, its coronary artery passages may be blocked to a very large extent. The cardioplegeia that had been injected through the aorta root may therefore, not be able to pass through these narrow artery passages. This may result in a non-homogeneous distribution of cardioplegia within the coronary arteries. To alleviate this potential problem, various methods have been employed which have sought to deliver cardioplegia directly (i.e in a retrograde manner) to the coronary sinus. These methods have chosen the coronary sinus because it is known that such coronary obstructive type diseases never occur in the coronary venous system and because such cardioplegic delivery, directly into the coronary sinus (which comprises a large vein), could provide for the desired homogeneous cardioplegic distribution.

One example of such a coronary sinus method requires the cannulation of the coronary sinus by directly injecting cardioplegic solution therein. This approach has many potential drawbacks. For example, placing a cannula within the coronary sinus has been found to be very difficult. Once the cannula has been placed within the coronary sinus it has been found to be equally as difficult to keep it in position for a length of time necessary to allow all of the cardiopelgia to be placed within the sinus. Such direct cannulation procedures may even cause extensive damage to the sinus itself. Lastly, it has been found that a relationship exists between the resultant homogeneity of cardioplegic distribution and the distance in which the cannula is placed within the sinus. Such a critical relationship evidences the fact that such a cannulation procedure might arguably produce poorer cardioplegic distributions than even the aforementioned aortic root technique.

Other presently used methods for introducing cardioplegia into the coronary venous system and more particularly into the coronary sinus itself, includes the steps of cannulating both the superior and inferior vena cavas; opening the right heart atrium; and then cannulating the coronary sinus under direct vision or manipulating the coronary sinus manually, with a cannula in place. These methods are extremely difficult to perform and again include the step of direct cannulation of the coronary sinus. They therefore suffer from the same drawbacks as was associated with the first method discussed (i.e. only requiring direct sinus cannulation). It is clear then, that an improved technique is needed to allow for the homogeneous distribution of cardioplegia within the coronary veins of a heart, even under such heart conditions such as coronary atherosclerosis. It is equally clear, that such a new and improved technique should avoid direct cannulation of the coronary sinus and should avoid the aforementioned problems and drawbacks associated with the prior techniques.

SUMMARY OF THE INVENTION

According to the teachings of the present invention, cardioplegia may be homogeneously distributed throughout the heart by having it enter the coronary veins through the coronary sinus. This homogeneous distribution is effected without directly cannulating or manipulating the sinus. Specifically, this invention provides for a cannula into which such cardioplegia may be introduced. The cannula of this invention, is generally placed within the right atrium cavity of the heart such that it extends into the inferior vena cava. The cannula contains a plurality of openings which communicate with both the inferior and superior vena cavas in order to transport blood contained therein to suitable oxygenating apparatus.

The cannula also contains sealing means for isolating a portion of the heart containing the coronary sinus. The sealing means of the cannula made in accordance with the preferred embodiment of this invention are inflatable balloons. The isolated portion of the heart is thereby substantially defined by the portion between the balloons. Cardioplegia is then injected from a source, through the cannula, and is output at an infusion port of the cannula which is also contained within the isolated heart portion. Once the cardioplegia has been introduced into the isolated heart portion it drains down into the coronary sinus, since the balloons prevent it from travelling outside of the isolated heart portion.

Once the cardioplegia is disposed within the coronary sinus it is homogeneously distributed throughout the coronary veins of the heart. Furthermore, this method and apparatus have been found to be relatively easy to use, relatively safe, and relatively reliable and do not require a direct cannulation and/or manipulation of the coronary sinus. This invention may also be used in addition to many other surgical techniques and associated apparatus such as a two stage venoatrial cannula which is commonly used during such heart surgery.

BRIEF DESCRIPTION OF THE DRAWINGS

The various advantages of the present invention will become apparent to those skilled in the art by reading the following specifications and by reference to the drawings in which:

FIG. 2 is a somewhat diagrammatic elevational view of a retrograde coronary sinus cardioplegia cannula made in accordance with the teachings of the preferred embodiment of this invention; and FIGS. 3–6, inclusive, are enlarged sectional views of a cannula made in accordance with the teachings of the preferred embodiment of this invention, as generally viewed from the lines 3—3, 4—4, 5—5, and 6—6, respectively in FIG. 2.

DESCRIPTION OF THE PREFERRED EMBODIMENTS

Figure 1:
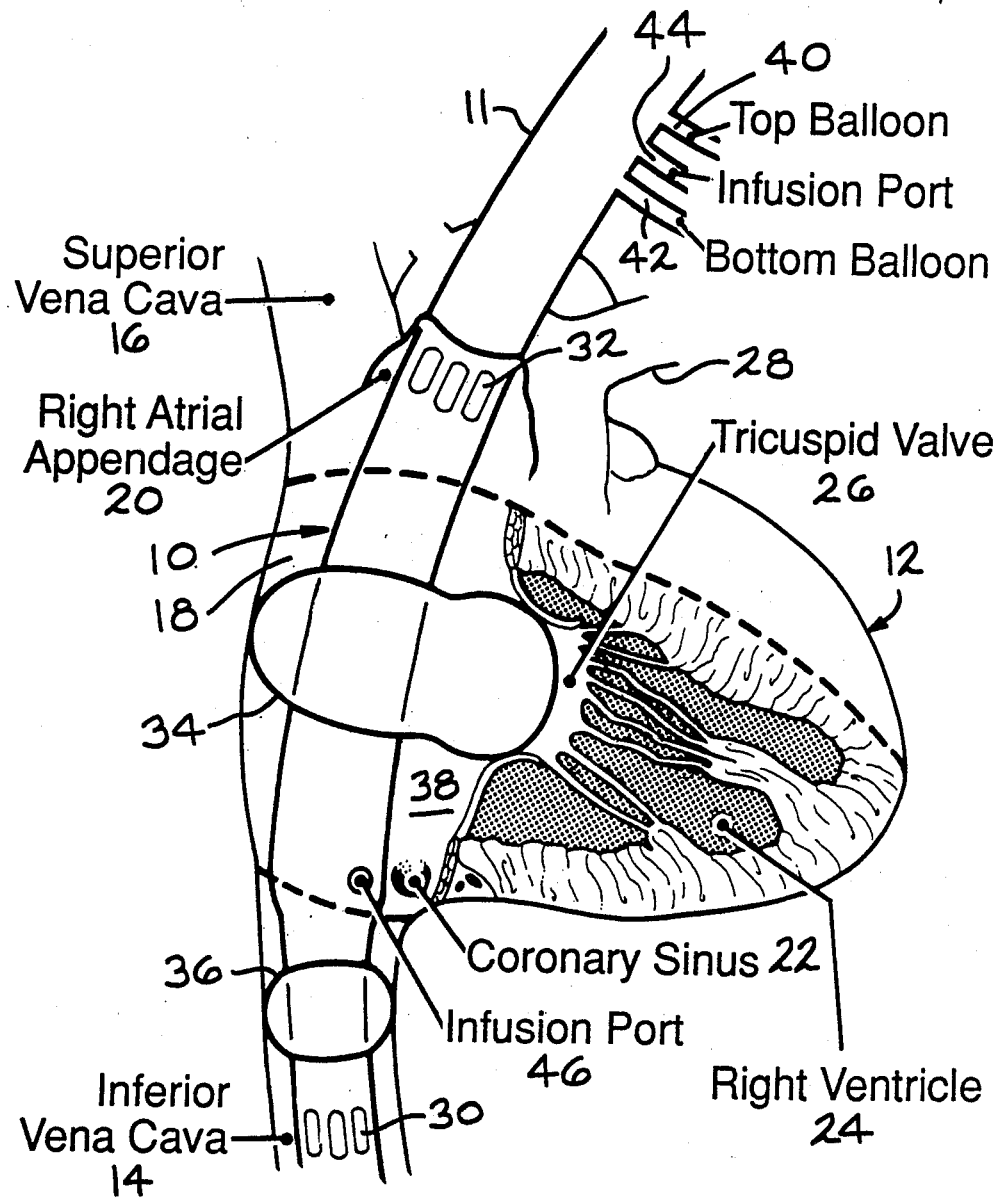
FIG. 1 is a diagrammatic view of a retrograde coronary sinus cardioplegia cannula made in accordance with the teachings of the preferred embodiment of this invention, shown generally disposed within a human heart.

Turning now to FIG. 1, a retrograde coronary sinus cardioplegia cannula 10 made in accordance with the teachings of this invention, is shown as including an elongated tubular body 11 projecting into and disposed within human heart 12. Further, heart 12 is shown as containing inferior vena cava 14, superior vena cava 16, right atrium cavity 18, right atrial appendage 20, coronary sinus 22, right ventrical 24, tricuspid valve 26, and pulmonary artery 28. Functionally, the inferior and superior vena cavas 14, 16 are large veins and serve to transport non-oxygenated blood from the lower and upper parts of the body respectively, to the heart 12. This non-oxygenated blood enters the right atrium cavity 18 and flows into right ventrical 24 through, and under the general control of, tricuspid valve 26. The non-oxygenated blood is subsequently pumped into the lungs through pulmonary artery 28 and is re-oxygenated and recirculated throughout the body. Right atrial appendage 20 serves as an entrance into right atrium cavity 18. Coronary sinus 22 represents a rather substantial vein and may be used to homogeneously distribute material to the coronary veins.

Cannula 10, as shown in FIG. 1, consists of a hollow tubular body 11 generally inserted into right atrial appendage 20 such that it extends into inferior vena cava 14 while traversing right atrium cavity 18. During heart surgery, a mechanical blood oxygenating apparatus is usually connected to heart 12 in order to oxygenate the blood contained within the inferior and superior vena cavas 14, 16. This apparatus must be used because heart 12 is substantially immobilized such that the de-oxygenated blood may not be pumped to the lungs in the manner previously specified. For this reason, cannula 10 contains a plurality of openings 30, 32 which allow for de-oxygenated blood contained within inferior and superior vena cavas 14, 16 to enter cannula 10 and be transported to such an oxygenating apparatus.

Cannula 10 also contains two inflatable balloons or seal members 34 and 36. These balloons 34, 36 when inflated serve to generally block inferior vena cava 24 and right atrium cavity 18 respectively, such that a portion of heart 12 is isolated. This isolated portion, shown as chamber 38, is thereby created such that coronary sinus 22 is the only substantial exit therefrom. Thusly, substantially all of the material contained within chamber 38 must exit only through coronary sinus 22. Balloon inflation ports 40, 42 control the inflation of balloons 34 and 36 respectively, by allowing for pressurized fluid, such as a liquid saline solution, to be transmitted to these balloons 34, 36. Further, cannula 10 contains infusion ports 44 and 46 which are associated with the introduction of material, such as cardioplegia, into chamber 38. Specifically, infusion port 44 is adapted to be coupled to a material source which, under pressure, may cause the material to enter cannula 10 through this infusion port 44. Infusion port 46 is placed generally within chamber 38. The material, thus introduced, travels through cannula 10 until it is output, through infusion port 46, into chamber 38. This material subsequently enter coronary sinus 22 and is homogeneously distributed within the coronary veins.

As shown in FIG. 2, the cannula body 11 contains a plurality of generally hollow passages 48, 50, and 52 running substantially along and extending longitudinally of the body 11. Specifically, passage 48 couples balloon inflation port 42 to balloon 36. Passage 52 couples balloon inflation port 40 to balloon 34. Passages 48 and 52 therefore enable injected fluid, such as a saline solution, to inflate balloons 36 and 34 respectively. A typical fluid source is shown in FIG. 2, as a syringe 54 having a plunger 56 and coupling means 58 such as a flexible tube. Upon engagement of plunger 56, coupling means 58 causes liquid to be input to balloon inflation port 42 thereby causing the inflation of balloon 36. Balloon 34 may be inflated in a similar manner through balloon inflation port 42.

Passage 50 couples infusion port 44 to infusion port 46 and allows for the placement of material, such as cardioplegia, into cavity 38. Typical material (i.e. cardioplegia) injecting means is also shown, in FIG. 2, as consisting of a syringe 60 containing a plunger 62 material 64 to be injected into cavity 38, and coupling means 66 such as a flexible tube. Upon engagement of plunger 62, coupling means 66 delivers material 64, which is under pressure, into infusion port 44 such that the material 64 traverses passage 50 and leaves cannula 10 through infusion port 46. Upon leaving infusion port 46, the material is within cavity 38.

Pressure monitor devices 68 and 70 may be coupled to cannula 10 in order to measure various pressures associated therewith. Pressure monitors such as the one shown diagrammatically at 68 may be coupled, either singularly or in combination with either a pressurized liquid source or material injecting means, to any of the balloon inflation ports 40, 42; or to infusion port 44. Additionally pressure monitor devices, such as shown such as the one shown diagrammatically at 70 in FIG. 2 may be coupled to cannula 10 such that the pressure associated with blood received from the inferior and superior vena cavas 14, 16 may be measured. Such pressure measurement, in general, is very important. For example, if the cardioplegia or other material is injected into cavity 38 at too great a pressure, substantial damage to the heart 12 may result.

From the above description, it is seen that this invention provides for a homogeneous distribution of material, such as cardioplegia within the heart passages. Furthermore, such homogeneous distribution is accomplished without cannulating or manipulating the coronary sinus in substantially any manner.

It is to be understood, however, that while the cannula 10 has been particularly described in connection with its use in infusing the heart passages with cardioplegia, the cannula 10 can also be used to evacuate material such as cardioplegia, from the heart passages. This is accomplished by simply connecting the part 44 to a vacuum pump or the like capable of creating a suction at port 46.

It will also be apparent that the preferred embodiments of the invention disclosed are well calculated to provide the advantages and the features above stated, and it will be appreciated that the invention is susceptible to modification, variation, and change without departing from the proper scope of fair meaning of the subjoined claims.

In the claims:

1. Cannula apparatus for delivering cardioplegia to the veins of the heart during cardiac surgery, said apparatus comprising a main tubular member adapted to be inserted into the right atrium cavity of the heart to a position extending into the inferior vena cava, said tubular member having spaced openings communicating with both the inferior and superior vena cavas, said openings being for the purpose of enabling blood to be oxygenated to enter the tubular member for transport to blood oxygenating apparatus, passage means operatively associated with said tubular member and having a discharge port located between said openings, said passage means having an inlet adapted to be connected to a source of cardioplegic solution, means forming a pair of fluid passages on said tubular member, a first inflatable seal member communicating with one of said fluid passages and being operable on inflation to block said inferior vena cavity around said tubular member, a second inflatable seal member communicating with the other one of said fluid passages and being operable on inflation to block the atrium cavity around said tubular member so as to form an isolated chamber around said tubular member and between said seal members communicating only with said discharge port for cardioplegic solution and the heart's coronary sinus thereby enabling a desired flow of cardioplegia to the coronary sinus from said isolated chamber so long as said seal members remain inflated.

2. A retrograde coronary sinus cannula for use in connection with a human heart particularly the portions of the heart identified as the tricuspid valve, the coronary sinus and the heart cavity communicating therewith, said cannula comprising a body member adapted to be inserted in said heart cavity for conducting blood to be oxygenated from the heart to an oxygenating station while the heart is inactive, inflatable seal members on said body member operable when inflated to isolate a chamber in the heart at a position adjacent the tricuspid valve and communicating with the coronary sinus, and means operatively associated with said body member forming a passage extending between said chamber and a location outside the heart, thereby enabling use of said passage to infuse fluid material into said chamber for subsequent flow into the coronary sinus which constitutes the sole outlet from the chamber or to withdraw fluid material from the heart through the coronary sinus and said chamber.

3. The cannula apparatus of claim 2 wherein said inflatable seal members are of a shape to seal against the portions of the heart around said body member in said heart cavity.

4. The cannula apparatus of claim 2 wherein said body member includes a plurality of fluid passages coupled to said inflatable seal members for use in inflating said seal members.

5. The method for causing material to enter a coronary sinus of a heart, said method comprising:
   (a) isolating a portion of said heart wherein said isolated portion contains said coronary sinus and said coronary sinus constitutes substantially the only outlet from said isolated portion; and
   (b) placing said material into said isolated portion of said heart whereby said material is caused to enter said coronary sinus.

6. The method of claim 5 wherein said heart also contains an inferior vena cava and a right atrium cavity and wherein said isolated portion of said heart is substantially defined by blocking said inferior vena cava and said right atrium.

7. The method of claim 6 wherein said blocking is accomplished by inflatable seal means positioned such that said coronary sinus constitutes the only substantial outlet from said isolated portion.

8. The method of claim 5 wherein said material comprises cardioplegia.

9. A method for delivering cardioplegia to the heart of a patient wherein said heart contains an inferior vena cava, superior vena cava, a right atrium cavity and a coronary sinus, said method comprising:
   (a) inserting a member into said right atrium such that said member is in communication with said inferior and superior vena cavas;
   (b) blocking said inferior vena cava and said right atrium around said member, such that an isolated portion of said heart is formed wherein, said coronary sinus constitutes the only substantial outlet from said isolated portion; and
   (c) infusing cardioplegia through said member such that said cardioplegia is made to flow into said isolated portion of said heart.

10. The method of claim 9 wherein said member is generally tubular and generally hollow.

11. A method for causing cardioplegia to enter a coronary sinus of a heart wherein, said heart also contains an inferior vena cava, superior vena cava and a right atrium and wherein, said method comprises:
   (a) inserting a member into said right atrium such that said member extends into said inferior vena cava and wherein, said member contains a plurality of openings in communication with said inferior and superior vena cavas and wherein, said member contains inflatable seal means for isolating a portion of said heart around said member, and wherein, said member contains input and output port means, in communication, for allowing material to enter and exit from said member;
   (b) activating said inflatable balloon means by injecting pressurized liquid into said member in order for said right atrium and said inferior vena cava to be blocked generally around said member, thusly forming an isolated portion of said heart wherein, said isolated portion contains said coronary sinus and said output port means and wherein, said coronary sinus constitutes the only substantial outlet from said isolated portion; and
   (c) placing cardioplegia into said input port means such that said cardioplegia is output from said member by said output means whereby, said cardioplegia is input to said isolated portion and enters said coronary sinus.

12. The method of claim 1 wherein said member is generally tubular and hollow.

* * * * *